June 10, 1947. R. G. JELLY Plant Pat. 737
ROSE PLANT
Filed May 31, 1946
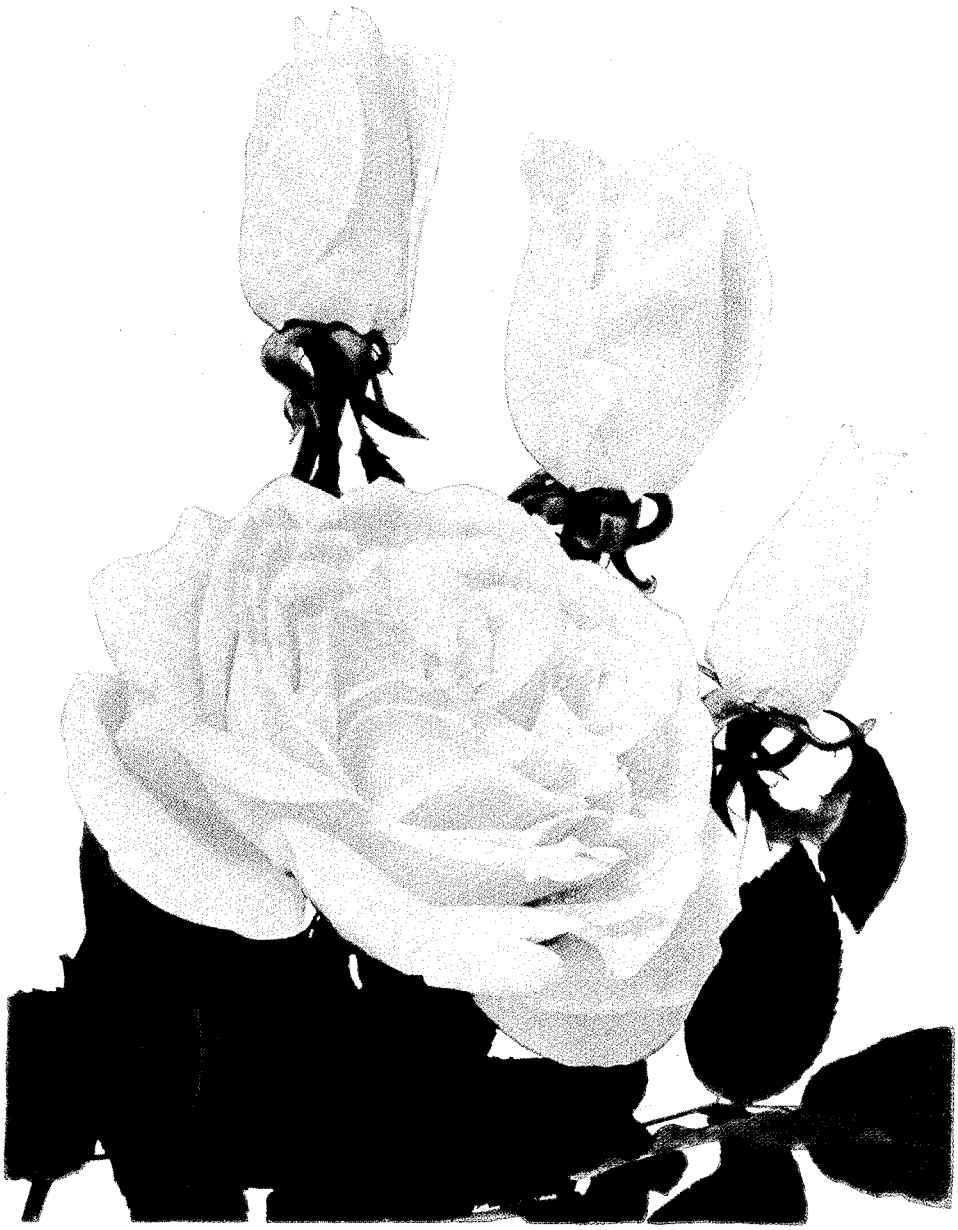
Inventor
R. G. Jelly
By Robb & Robb
His attorneys Patented June 10, 1947

UNITED STATES PATENT OFFICE

737

ROSE PLANT

Robert G. Jelly, Richmond, Ind., assignor to The E. G. Hill Company, Richmond, Ind., a corporation of Indiana Application May 31, 1946, Serial No. 673,312

1 Claim. (Cl. 47—61)

This invention relates to a new and distinct variety of hybrid tea rose plant, resulting from a cross of the two varieties "R. M. S. Queen Mary" (Pl. Pat. 249) and "Eternal Youth" (Pl. Pat. 332).

This new rose is dominantly characterized as to novelty by the extremely long, gracefully pointed form of the bud, and its delicate pink color with a brilliant yellow base. As the bud opens, the color on the inside of the petals, which is much deeper than the reverse, reveals a full-blown flower of brilliant pink much darker than that of the bud.

Further, the flower, when mature, is very large, being in some instances seven inches in diameter.

The plant itself is upright in growth and the flowers are borne on long, stiff stems. Its foliage is large and dark green in color, which as a background, lends to the general attractiveness of the cut flower.

This new variety is not similar to any known variety, but it can best be compared to its seed parent, from which it has inherited its long pointed bud, while from its pollen parent it derives its fire and brilliance of color, thereby combining very desirable characteristics of the parents, quite favorable to the new rose either as a forcing greenhouse or garden variety.

The drawing illustrates specimens of this new variety including the foliage and the blooms at different stages of development from bud to full blown flower.

The following is a detailed description of the new variety, color terminology being in accord with Ridgway's Color Standard, except where otherwise indicated by ordinary dictionary definition:

Type: Tall; greenhouse; seedling; for cut flowers.
Class: Hybrid tea.
Breeding: At Richmond, Indiana. Seedling.
*Seed parent.*—"R. M. S. Queen Mary."
*Pollen Parent.*—"Eternal Youth."
Propagation: Holds its distinguishing characteristics through succeeding propagations by cuttings, grafting, and budding. (Layering not observed.)

*Flower*

Locality where grown: Richmond, Indiana.
Flowers borne: Singly; on strong, long stems.
Quantity of Bloom: Moderate in greenhouse.
Continuity: Continuous.
Fragrance: Moderate.

Bud:
*Peduncle.*—Medium size; medium heavy; erect; light green; rough; numerous red prickles.
*Before calyx breaks.*—*Size*—large. *Form*—long, with a conspicuous neck; with foliaceous appendages on the surface of the bud; with slender foliaceous parts extending beyond the tip of the bud equal to ½ or more of its length.
*As calyx breaks.*—*Color*—petal except for base, Alizarine Pink, Plate XIII; petal at base, Wax Yellow, Plate XVI.
*As first petal opens.*—*Size*—large. *Form*—very pointed. *Color* — outside, Alizarine Pink, Plate XIII; inside, Rose Color, Plate XII.
*Opening.*—Opens up well.
Bloom:
*Size.*—When fully open, very large; six to seven inches.
*Petalage.*—Double; from 30 to 35 petals arranged regularly.
*Form.*—Full high center at first; becoming open cupped; petals remaining at first very tightly rolled inward; becoming later, at maturity, very loosely flat cupped.
Petals: Thick; with inside and outside satiny.
*Shape.*—Outside—obovate; apex is flat ending in minute point. Intermediate—obovate; apex is flat ending in minute point. Inside—obovate; apex is flat ending in minute point. Inside—obovate; apex is flat ending in minute point.
*Color.*—Shaded.

This description of a newly opened flower was made from a rose grown in a greenhouse in the month of February, 1946, at Richmond, Indiana:

*Color.*—*Outside petal*—outside surface—Alizarine Pink, Plate XIII; inside surface—Rose Color, Plate XII. *Intermediate petal*—outside surface — Alizarine Pink, Plate XIII; inside surface—Rose Color, Plate XII. *Inner petal*—outside surface—Alizarine Pink, Plate XIII; inside surface—Rose Color, Plate XII.

This description was made from a rose that was open for three days in a greenhouse in the month of February, 1946, at Richmond, Indiana:

*Outside petal.*—outside surface — Venetian Pink, Plate XIII; inside surface—Deep Rose Pink, Plate XII.

*Inside petal*—outside surface—Alizarine Pink, Plate XIII; inside surface—Deep Rose Pink, Plate XII.

*General color effect.*—Newly opened flower—Light Pink. Three days open—deeper shade than in bud.

*Behavior.*—Persist; fading brown. Petals burn in hot weather in greenhouse.

*Flower longevity.*—Kept at living room temperatures—5 days in February.

*Reproductive organs*

Stamens: Medium size; arranged regularly about pistils.
Filaments: Long; reddish; with anthers.
Anthers: Large; Yellow; all open at once.
Pollen: Abundant; Gold Yellow.
Pistils: Medium number.
Styles: Uneven; medium long; medium heavy; separated.
Stigma: Yellow.
Ovaries: All enclosed in calyx.
Sepals:
*Inside.*—Gray Green.
*Outside.*—Dark Green.

*Plant*

Foliage:
*Leaves.*—Composed of 5 to 7 leaflets; abundant; large; leathery.
*Leaflets.*—Shape—ovoid, with apex acute, base round, margin simply serrate.
*Color.*—*Mature*—upper surface, dark green; under surface, moderately Gray Green.

*Young*—upper surface—moderately light Green; under surface—moderately light Green.

*Rachis (the supporting stem of the compound leaf).*—Medium heavy. Upper side, smooth grooved; under side, sparsely thorny.

*Stipules.*—Medium length; moderately narrow; with moderately short points, turning out at an angle of 45°.

Growth:
*Habit.*—Upright.
*Growth.*—Moderately free.
*Canes.*—Medium heavy.
*Main stems.*—Bright Green. *Thorns*—several; long; straight; with long narrow base, Red in color. *Prickles*—several; Green in color. *Hairs*—none.
*Branches.*—Bright green. *Thorns*—Bright green. *Prickles*—Bright green.
*New shoots.*—Bright Green. *Thorns*—several. *Prickles*—several; Green. *Hairs*—none.

I claim:

A new and distinct variety of rose plant, characterized as to novelty by its extremely long, gracefully pointed bud, of delicate pink color with brilliant yellow base; the deeper pink coloring of the full blown flower and its very large size; the upright growth of the plant with dark green foliage and its habit of producing such flowers singly on long, stiff stems, substantially as shown and described.

ROBERT G. JELLY.